(12) United States Patent
Reinke et al.

(10) Patent No.: US 8,706,520 B2
(45) Date of Patent: Apr. 22, 2014

(54) METADATA TAGGING SYSTEM FOR A DIABETES MANAGEMENT SYSTEM OF DEVICES

(75) Inventors: Robert E. Reinke, Indianapolis, IN (US); Phillip E. Pash, Indianapolis, IN (US); James R. Long, Fishers, IN (US); Guido Konrad, Bern (CH); Erich Imhof, Utzenstorf (CH); Gerhard Frisch, Edingen-Neckarhausen (DE)

(73) Assignees: Roche Diagnostics Operations, Inc., Indianapolis, IN (US); Roche Diagnostics International AG, Steinhausen (CH)

( * ) Notice: Subject to any disclaimer, the term of this patent is extended or adjusted under 35 U.S.C. 154(b) by 262 days.

(21) Appl. No.: 12/905,468

(22) Filed: Oct. 15, 2010

(65) Prior Publication Data

US 2012/0095774 A1    Apr. 19, 2012

(51) Int. Cl.
*G06Q 10/00*  (2012.01)
*G06Q 50/00*  (2012.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

| | | | | |
|---|---|---|---|---|
| 6,168,563 B1* | 1/2001 | Brown | ........................... | 600/301 |
| 6,334,778 B1* | 1/2002 | Brown | ........................... | 434/258 |
| 6,368,273 B1* | 4/2002 | Brown | ........................... | 600/300 |
| 6,381,577 B1* | 4/2002 | Brown | ............................. | 705/2 |
| 7,073,193 B2* | 7/2006 | Marsh | ........................... | 725/114 |
| 7,103,578 B2* | 9/2006 | Beck et al. | ........................ | 705/75 |
| 7,246,163 B2* | 7/2007 | Tindal | ........................... | 709/223 |
| 7,363,649 B2* | 4/2008 | Marsh | ........................... | 725/114 |
| 7,467,164 B2* | 12/2008 | Marsh | ................................ | 1/1 |
| 7,516,192 B2* | 4/2009 | Brown | ........................... | 709/217 |
| 7,533,171 B2* | 5/2009 | Brown | ........................... | 709/224 |
| 7,624,028 B1* | 11/2009 | Brown | ............................. | 705/3 |
| 2003/0195863 A1* | 10/2003 | Marsh | ............................. | 707/1 |
| 2004/0003403 A1* | 1/2004 | Marsh | ............................ | 725/53 |
| 2005/0192987 A1* | 9/2005 | Marsh | ........................... | 707/100 |

(Continued)

OTHER PUBLICATIONS

Garcia-Saez G. et al: "Architecture of a wireless Personal Assistant for telemedical diabetes care", International Journal of Medical Informatics, Elsevier Scientific Publishers, Shannon, IR, vol. 78, No. 6, Jun. 1, 2009, pp. 391-403, XP026044113, ISSN: 1386-5056, DOI: 10.1016/J.IJMEDINF.2008-12-003.

(Continued)

*Primary Examiner* — Michael Fuelling
(74) *Attorney, Agent, or Firm* — Harness, Dickey (57) ABSTRACT

A diabetes management system having a reliable data management scheme is disclosed. The system comprises a plurality of devices, each device performing a different function relating to treatment of diabetes. Each device has a device identifier and generates data records. Each device includes a metadata generator configured to generate a metadata tag for a data record generated by the device. A metadata tag includes the device identifier of the corresponding device, a record identifier, and a source identifier indicating whether the record was originated by a human or the device. The system further includes a diabetes management device. When a device generates a new record, the metadata generator generates a new record identifier and a new metadata tag based on the new record identifier and the device identifier of the device. The first device propagates the new record and the new metadata tag to the diabetes management device.

7 Claims, 5 Drawing Sheets

(56) References Cited

U.S. PATENT DOCUMENTS

| | | | |
|---|---|---|---|
| 2006/0004611 A1* | 1/2006 | Brown | 705/3 |
| 2006/0010014 A1* | 1/2006 | Brown | 705/2 |
| 2006/0247979 A1* | 11/2006 | Brown | 705/26 |
| 2006/0259201 A1* | 11/2006 | Brown | 700/291 |
| 2006/0271404 A1* | 11/2006 | Brown | 705/2 |
| 2006/0285660 A1* | 12/2006 | Brown | 379/88.02 |
| 2007/0005653 A1* | 1/2007 | Marsh | 707/104.1 |
| 2007/0061167 A1* | 3/2007 | Brown | 705/2 |
| 2007/0156457 A1* | 7/2007 | Brown | 705/2 |
| 2007/0156892 A1* | 7/2007 | Brown | 709/224 |
| 2007/0168242 A1* | 7/2007 | Brown | 705/7 |
| 2007/0213603 A1* | 9/2007 | Brown | 600/300 |
| 2007/0213604 A1* | 9/2007 | Brown | 600/300 |
| 2007/0213605 A1* | 9/2007 | Brown | 600/300 |
| 2008/0033767 A1* | 2/2008 | Brown | 705/4 |
| 2008/0097180 A1* | 4/2008 | Brown | 600/365 |
| 2008/0097181 A1* | 4/2008 | Brown | 600/365 |
| 2008/0103377 A1* | 5/2008 | Brown | 600/347 |
| 2008/0103379 A1* | 5/2008 | Brown | 600/365 |
| 2008/0103380 A1* | 5/2008 | Brown | 600/365 |
| 2008/0109172 A1* | 5/2008 | Brown | 702/19 |
| 2008/0109197 A1* | 5/2008 | Brown | 703/11 |
| 2009/0150484 A1* | 6/2009 | Roberts | 709/203 |

OTHER PUBLICATIONS

Part 20601: Application Profile—Optimized Exchange Protocol, IEEE Std 11073-20601 Sep. 26, 2008.

Part 10417: Device Specialization-Glucose Meter, IEEE Std 11072-10417, May 8, 2009.

Continua Design Guidelines 2010, Oct. 1, 2010.

* cited by examiner

METADATA TAGGING SYSTEM FOR A DIABETES MANAGEMENT SYSTEM OF DEVICES

FIELD

The present disclosure relates generally to medical devices and more particularly to a system for tagging metadata for data being communicated between devices in a diabetes management system.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin and all other factors affecting blood glucose often require a person with diabetes to forecast blood glucose levels. Therefore, therapy in the form of insulin, oral medications, or both can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise, and lifestyle. Lab test results include HbA1C, cholesterol, triglycerides, and glucose tolerance. Healthcare professional recommendations include prescriptions, diets, test plans, and other information relating to the treatment of the patient.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

Additionally, to effectively manage the care and health of the patient, there is a need for a means to reliably manage data records from the other medical devices. As the system of devices communicating with one another becomes more complex, a technical problem arises in trying to keep data records consistent, especially when patients are provided with the ability to enter and edit records manually. Accordingly, a system for tagging records with metadata that ensures unique metadata tags is described herein. Based on metadata tagging scheme, data records transmitted between the devices may remain consistent and confusion of data can be avoided.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In one aspect of the disclosure, a diabetes management system having a reliable data management scheme is disclosed herein. The diabetes management system includes a plurality of devices, each device performing a different function relating to treatment of diabetes of a patient and having a device identifier that identifies a type of the device. Each device generates data records relating to the function of the device, and each device includes a metadata generator configured to generate a metadata tag for a data record generated by the device. The metadata tag includes the device identifier of the corresponding device, a record identifier, and a source identifier indicating whether the record was originated by a human or a device. The system further comprises a diabetes management device in electronic communication with the plurality of devices, wherein the diabetes management device is configured to manage records received from the plurality of devices. When a first device of the plurality of devices generates a new record to be communicated to the diabetes management device, the metadata generator of the first device generates a new unique record identifier and a new metadata tag based on the new unique record identifier and the device identifier of the first device, and the first device propagates the new record and the new metadata tag to the second device.

In a second aspect of the disclosure, a diabetes management system having a reliable data management scheme, the system comprising a first device performing a first function relating to treatment of diabetes and having a first device type identifier associated thereto and a diabetes management device in communication with the first device. The first device has associated therewith: a) a record generation module that generates a record relating to the first function or relating to operating conditions of the first device, b) a metadata generator that generates a new metadata tag for tagging the record, wherein the new metadata tag includes the first device type identifier, a record identifier that is a unique value associated with the first record, and a source identifier indicating whether the record was originated by a human or the first device; and c) a communication interface that allows the first device to communicate with a communication interface of the diabetes management device, wherein when the first device is to transmit the record to the diabetes management device, the first metadata generator generates the new metadata tag and the communication module transmits the record and the new metadata tag to the diabetes management device. The new metadata tag is associated with the record for the duration of the record.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
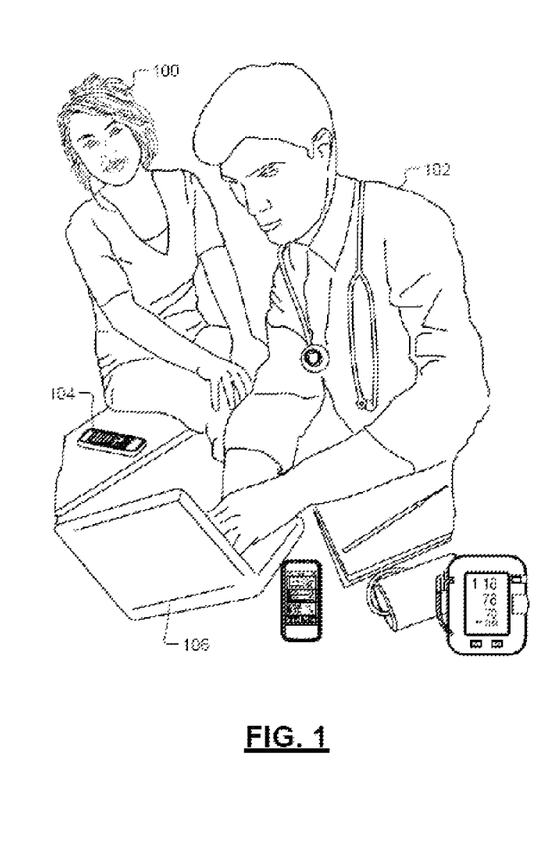
FIG. 1 shows a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
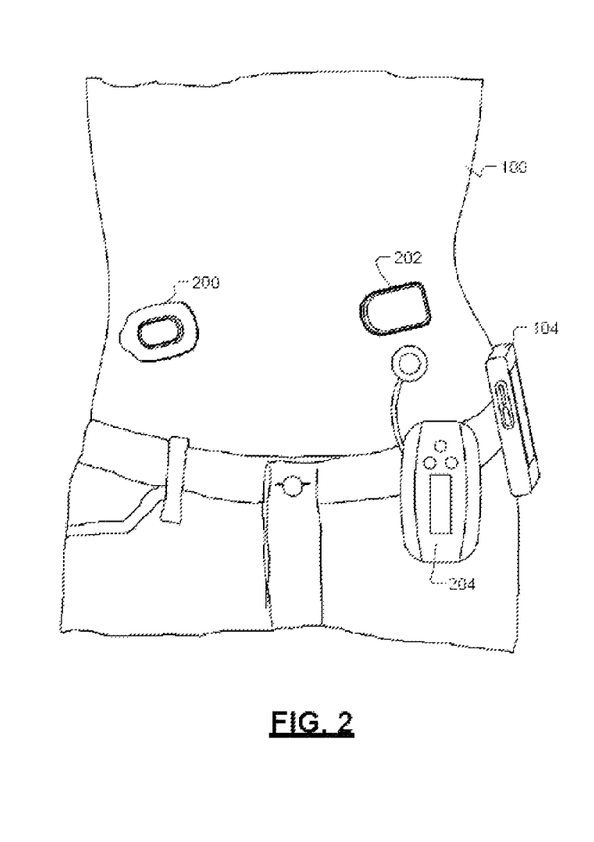
FIG. 2 shows a patient with a continuous glucose monitor (CGM), ambulatory durable insulin infusion pump, ambulatory non-durable insulin infusion pump, and diabetes manager.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the handheld diabetes management device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
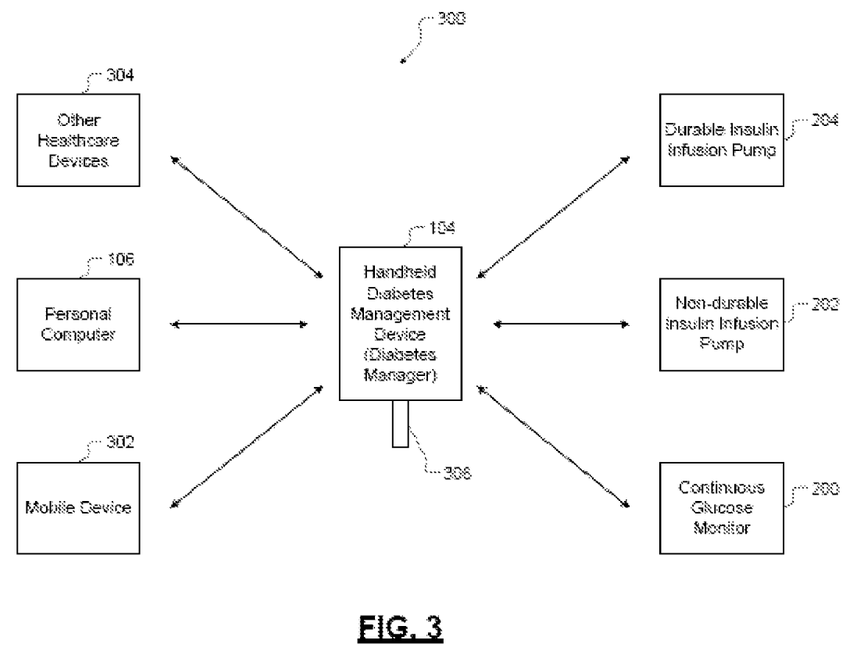
FIG. 3 shows a diabetes care system of systems used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using a proprietary Gazell wireless protocol developed by Nordic Semiconductor, Inc.

Additionally, the diabetes manager 104 includes a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a PDA, or a pager. The diabetes manager 104 can send messages to an external network through the mobile device 302. The mobile device 302 can transmit messages to the external network based on requests received from the diabetes manager 104.

Figure 4:
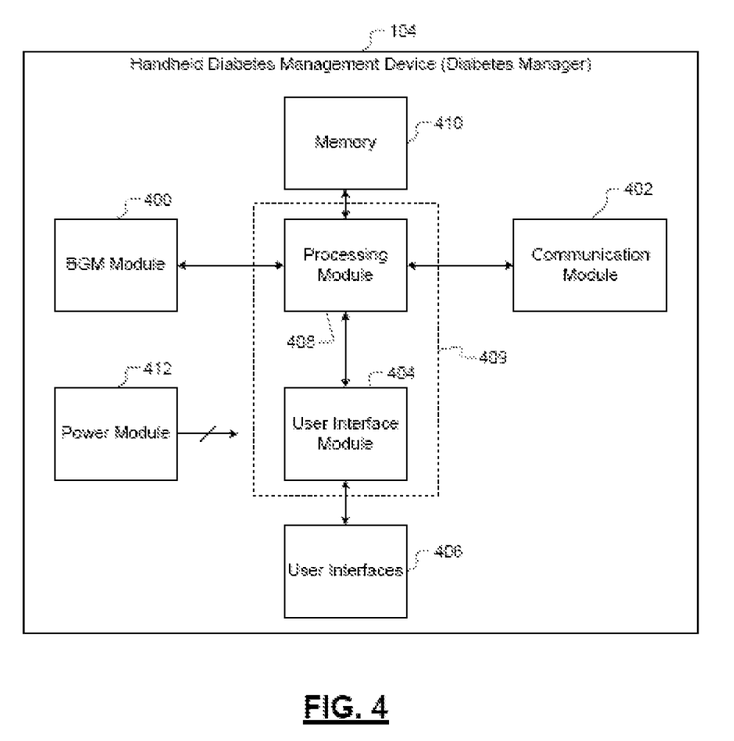
FIG. 4 shows a high level diagram of a diabetes care system-of-systems architecture.

Referring now to FIG. 4, the diabetes manager 104 comprises a blood glucose measuring (BGM) module 400, a communication module 402, a user interface module 404, user interfaces 406, a processing module 408, memory 410, and a power module 412. The BGM module 400 includes a blood glucose measuring engine that analyzes the sample provided by the patient 100 on the blood glucose measuring strip 306 and that measures the amount of blood glucose in the sample. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. of the diabetes manager 104 (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

Figure 5:
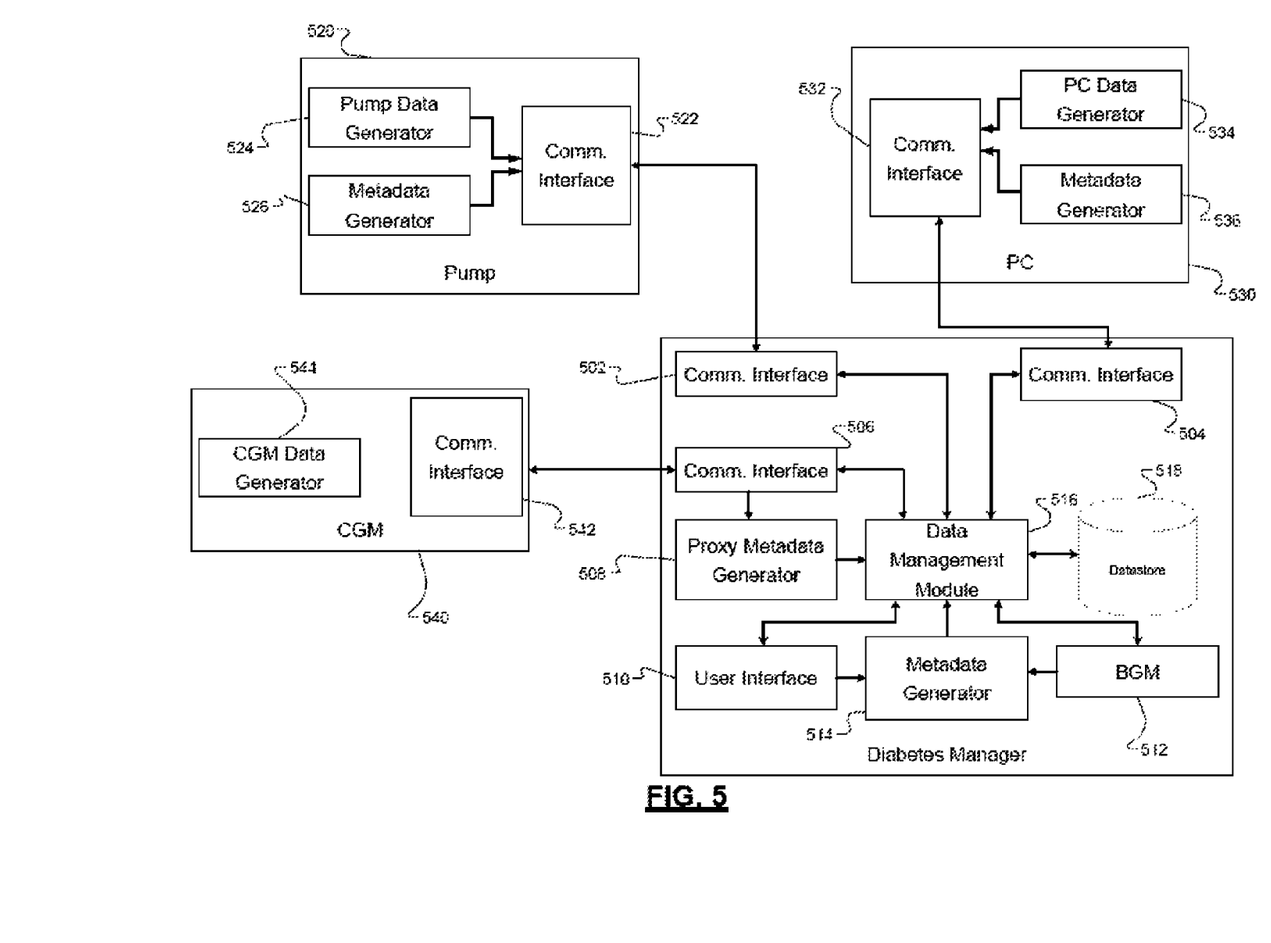
FIG. 5 shows components of a system of devices that are configured to communicate data records and corresponding metadata tags with one another.

FIG. 5 illustrates a diabetes manager 500 and a plurality of devices, each device performing a different function relating to treatment of diabetes of a patient. The devices include a CGM 540, an insulin pump 520, and a PC 530. It is envisioned, however, that the system can include more or less devices. The diabetes manager 500 includes a plurality of communication interfaces 502, 504 and 506, that receive data records from the plurality of devices. Depending on the transmitting device, the received data records can include a metadata tag. A metadata tag is additional data, stored with the data record, which provides additional information to a data management module 516. A metadata item is a contiguous set of byes within a data record that gives the value for a property of the data record. The metadata tag includes a device identifier of the device which generated the data, a record identifier, and a source identifier which indicates whether the record was originated by the patient, the device, or a third party. An exemplary structure of a metadata tag with exemplary metadata items is provided below:

```
Metadata tag{
    data_record_type;
    device_identifier;
    record_identifier;
    source_identifier;
    time_stamp;
    last_modification;
    checksum;
}
```

As discussed, the diabetes manager 500 is in communication with the plurality of devices, such that data records are transferred from the devices to the diabetes manager 500 and to the devices from the diabetes manager 500. The diabetes manager 500 relies on data received from the various devices to manage the treatment of the patient's diabetes. Thus, an issue arises when data received from more than one source and the received data is inconsistent. Further, there is a need for a reliable way to resolve such inconsistencies, as medical decisions can be derived from the received data.

For example, a patient can enter, via user interface 512, that a first amount of insulin was delivered at a specific time. The insulin pump 520, however, may transmit a record indicating that a second amount of insulin was delivered at the same time. The diabetes manager 500 needs to be able to determine the source of the inconsistent records as well as to know which record to base a future decision on in the future. The metadata tags discussed above provide a solution to these problems. As will be described below, each device has a metadata generator associated therewith that generates metadata to allow a data management module 516 to manage the data records received from various sources.

An exemplary insulin pump 520 is comprised of a pump data generator 524, a metadata generator 526, and a communication interface 522. The pump data generator generates records relating to the administration of insulin to a patient and records relating to the operational state of the insulin pump 520. The insulin pump 520 can also have a user interface which allows a patient to enter additional data relating to the administration of the patient's insulin. Thus, the pump data generator 524 can be further configured to generate data records pertaining to the patient entered data.

The metadata generator 526 of the insulin pump generates metadata tags for data records that are transmitted to another device, e.g. the diabetes manager 500. When the pump data generator 524 generates a new pump data record, the metadata generator 526 receives a request to generate a metadata tag. The metadata tag can be a data structure with predefined metadata items. The predefined metadata items can include the device, record, and source identifiers, as well as a time-stamp, a time of last modification, and a cyclic redundancy check or checksum. The device identifier is a static value indicating the identity of the pump. The device identifier is a bit string representing numerical values, character values, or a combination of both. In some embodiments, the device identifier is an unsigned 32-bit value that uniquely identifies the device from all other devices in the plurality of devices. Further, the device identifier can be a generic identifier of a particular type of pump, specific to the brand of pump, unique to the particular pump, or a combination thereof.

The record identifier is a value generated by the metadata generator 526. Each time the metadata generator 526 generates a record identifier, the value should be a new value. Thus, in some embodiments the metadata generator 526 implements a counter that is incremented every time a new record is generated. For instance, the first record generated by the pump data generator 524 will have a record identifier of 1. The following record will have a record identifier of 2, and so on and so forth. The record identifier can also include character values. In some embodiments, the record identifier is an unsigned 32-bit value that the device will not reproduce for any subsequent records it produces. It is envisioned that other means of generating a record identifier can also be implemented. Together, the device identifier and the record identifier constitute a unique number for the record, regardless of the device generating the data record.

The metadata generator 526 also generates a source identifier that indicates whether the record was originated by the pump or by a human. This can be a one-bit flag, or can further indicate whether the record was generated by the patient or a third party, e.g. a clinician.

The metadata generator 526 can further populate additional metadata items in the metadata tag, including the time stamp and the time that the record was last modified. It is appreciated that the time that a record was last modified can be initially set equal to the time stamp, and another device can change the value of the time that a record was last modified. It is noted that the time can be relative or absolute time. The metadata generator can further include a metadata item indicating of what type of record it is, e.g. insulin pump record or insulin pump error record.

The metadata generator 526 can also calculate a checksum value using a predetermined function. The checksum is a function of the value in the data record. The validity of the data record can later be verified by applying the predetermined function to the stored data record and comparing the result to the received checksum.

Once a metadata tag is generated, the communication interface 522 of the insulin pump 520 can transmit the pump data record and the metadata tag to a communication interface of another device, such as the communication interface 502 of the diabetes manager 500.

The PC 530 generates patient data. As mentioned above, the PC 530 executes diabetes analysis software. This software can receive input from the patient or other devices, e.g. the diabetes manager 500. Based on various data, the PC data generator 534 will generate a PC data record.

When a PC data record is generated, a metadata generator 536 of the PC 530 will generate a metadata tag in a manner similar to that of the metadata generator 526 of the insulin pump 520. The metadata generator 536 will provide the metadata items of the metadata tag, including a device indicator, i.e. a value that indicates that the PC generated the data record, a record identifier, and a source identifier. The metadata generator 536 can implement a counter similar to the one described above. Of note, both the PC and the insulin pump (or any other device) can generate metadata tags whose record identifiers have equal values because the device identifier in each metadata tag will be different. The metadata tag can also include metadata items indicating a time-stamp, a field indicating a time of last modification, a record type indicator, and a checksum.

After a PC data record and corresponding metadata tag have been generated, the communication interface 532 of the PC 530 communicates the PC data record to a corresponding communication interface 504 of the diabetes manager 500.

Some devices do not have the requisite computational resources to generate metadata tags. For instances, a CGM 540 may lack the resources to generate a metadata tag each time it transmits a CGM measurement. In these embodiments, the CGM 540 monitors the patient's glucose levels and transmits the CGM measurements without any metadata. The CGM data generator generates CGM data records indicating the CGM measurements or operational conditions of the CGM and the communication interface of the CGM 542 transmits the CGM data records to a corresponding communication interface 506 of the diabetes manager 500. A proxy metadata generator 508 residing on the diabetes manager 500, however, generates metadata tags corresponding to the CGM data records. The proxy metadata generator 508 generates metadata tags in the manner described above. The proxy metadata generator 508 will associate the device identifier of the CGM 540 and will implement an independent counter for generating the record identifier for the CGM data records. As the CGM 540 does not have a user interface, all records will be classified as being machine generated. The time stamp provided to the metadata tag can be the time that the CGM data record is received. While a lack of computational resources is cited as a reason for including a proxy metadata generator 508, the decision does not need to be based on the computational resources of the transmitting device.

The diabetes manager 500 also generates data records. For instance, an exemplary diabetes manager 500 includes a user interface 510 and a blood glucose monitor (BGM) 516, both of which can generate data records. The BGM 516 generates BG data records. The user interface 510 receives patient input which is used to generate patient data records. The metadata generator 504 of the diabetes manager receives an instruction from the user interface 510, the BGM 516, or any other data generating component of the diabetes manager 500. The metadata generator 514 generates a metadata tag having metadata items indicating a device identifier of the diabetes manager 500, a record identifier, and a source identifier. If the data record originates from the user interface 510 based on the input of the patient, then the source identifier can indicate that the patient data record is human-generated. If the BGM 516 generates a data record based on an automated bG reading, then the source identifier can indicate that the BGM data record is machine generated. Additional metadata items, such as record type, time stamp, time of last modification, and checksum can also be recorded in the metadata tag.

The data management module 516 receives the data records from the various data sources and stores them in the datastore 518 of the diabetes manager 500. The datastore 500 can have one or more databases stored thereon. The data management module 516 uses a data record and the corresponding metadata tag to generate an entry in the database or to modify an entry in the database.

The exemplary data management module 516 is further configured to resolve conflicts between two data records. To resolve conflicts, the data management module 516 adheres to a set of predetermined rules for resolving data conflicts. An exemplary rule is that a machine-generated record receives precedence over a human-generated value. For instance, in the example above, the patient and the insulin pump can provide two different values for an amount of insulin delivered at a specific time. In this case, the data management module 516 will enter the machine-generated value in the database entry, unless there is an indication of an error, e.g. a checksum value in the metadata does not match a computed checksum value based on the values in the data record. Another exemplary rule is that a later modification of a record gains precedence over an earlier entered modification. For example, if a patient enters meal information indicating that he ate 500 carbohydrates at breakfast, then later changes that value to 800, the later value is stored in the database. It is envisioned that other rules can be implemented by the data management module 516 for maintaining data consistency throughout the system of devices.

While the foregoing describes the situation where all data records are transmitted to the diabetes manager 500, it is noted that data records can be transferred to the devices from the diabetes manager 500 as well. For instance, the diabetes manager 500 can communicate data records to the PC 530. The PC 530 can also have a data management module that ensures data records are consistent between the PC 520 and the diabetes manager 500.

Figure 6:
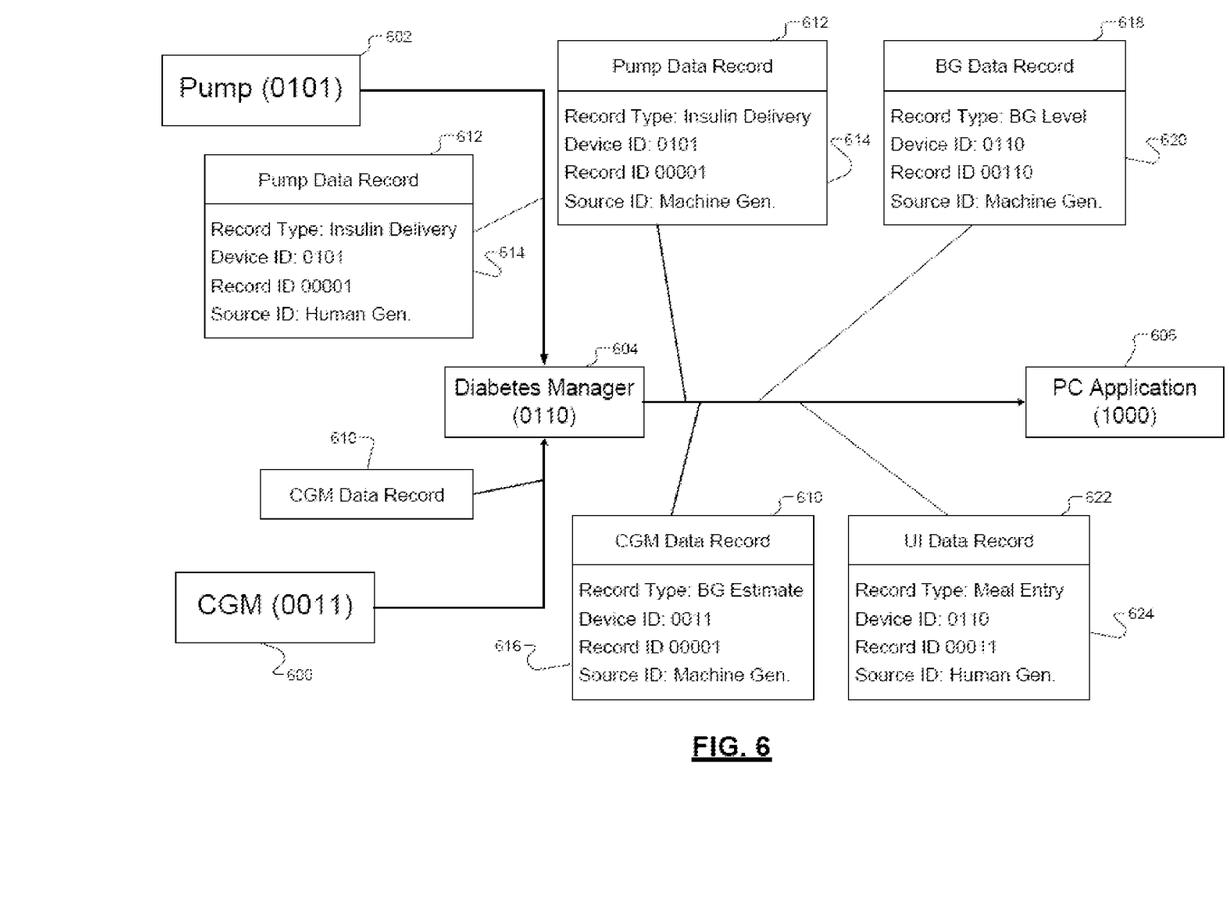
FIG. 6 shows an example of data records and metadata tags being communicated throughout a system of diabetes treatment devices.

FIG. 6 illustrates an example of data records and corresponding metadata tags being transmitted throughout the system of devices. In the example, a CGM 600 and an insulin pump 602, transmit CGM data records 610 and pump records 612, respectively, to a diabetes manager 604. As shown, the CGM data record is initially transmitted without a metadata tag, while the pump record has a metadata tag 614. The diabetes manager 604 passes the CGM data record 610 and pump record 612 to the PC 606. The diabetes manager 604 has generated a metadata tag 616 on behalf the CGM 600 to accompany the CGM record 610. Note that the device ID and the record ID of both the CGM data record 610 and the pump data record 612 are not altered when transmitted from the diabetes manager 604 to the PC 606. The diabetes manager 606 has also generated a BG data record 618 and a UI record 622, as well as corresponding metadata 620 and 624 respectively. Note that both records have the same device ID, as both were generated by the diabetes manager 600.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A diabetes management system having a reliable data management scheme, the system comprising:
   a first device performing a first function relating to treatment of diabetes, the first device having a first device type identifier associated therewith;
   a diabetes management device in communication with the first device and a continuous blood glucose monitor, the diabetes management device having a diabetes manager device type identifier associated therewith;
   the continuous glucose monitor including a subcutaneous sensor that monitors an amount of glucose in a body fluid of a patient and a continuous glucose monitor data generator that generates a continuous glucose monitor data record indicating the amount of glucose sensed by the subcutaneous sensor, the continuous glucose monitor transmitting the continuous glucose monitor data record to the diabetes management device, wherein the continuous glucose monitor has a continuous glucose monitor device type identifier associated therewith;
   wherein the first device includes:

a) a first device record generation module that generates a first record relating to the first function or relating to operating conditions of the first device;

b) a first device metadata generator that generates a new metadata tag for tagging the first record, wherein the new metadata tag includes the first device type identifier, a first record identifier that is a unique value associated with the first record, and a first source identifier indicating whether the first record was originated by a human;

c) a communication interface that allows the first device to communicate with the diabetes management device, wherein when the first device is to transmit the first record to the diabetes management device, the first metadata generator generates the new metadata tag and the communication module transmits the first record and the new metadata tag to the diabetes management device; and wherein the diabetes management device includes:

a) a diabetes manager record generation module that generates a diabetes manager record;

b) a diabetes manager metadata generator that generates a diabetes manager metadata tag for tagging the diabetes manager record, wherein the diabetes manager metadata tag includes the diabetes manager device type identifier, a diabetes manager record identifier that is a unique value associated with the diabetes manager record, and a diabetes manager source identifier indicating whether the diabetes manager record was originated by the diabetes management device or the human;

c) a proxy metadata generator that generates a continuous glucose monitor data record metadata tag for tagging the continuous glucose monitor data record received from the continuous glucose monitor, wherein the continuous glucose monitor data record metadata tag includes the continuous glucose monitor device type identifier and a continuous glucose monitor data record identifier corresponding to the continuous glucose monitor data record.

2. The diabetes management system of claim 1 wherein the first device is one of an insulin pump and a PC executing diabetes management software.

3. The system of claim 1 wherein the diabetes management device includes a data management module that manages first data records received from the first device, the data manager data records, and the continuous glucose monitor data records according to a set of predetermined rules.

4. The system of claim 3 wherein the set of predetermined rules include a rule which provides priority to data manager data records having source identifiers indicating that the data records were not originated by a human over data manager data records having source identifiers indicating that the data records were originated by the human.

5. The system of claim 1 wherein the diabetes management device has a blood glucose monitor housed therein, wherein the blood glucose monitor generates blood glucose records and the diabetes manager metadata generator further generates metadata tags for the blood glucose records, wherein the device identifier of the metadata tags for the blood glucose records is the device identifier of the diabetes management device.

6. The system of claim 1 wherein a particular metadata tag includes a checksum value that is determined using a predetermined function that uses contents of a particular data record at a time of creation as input, wherein validity of the particular data record can be verified by calculating a checksum check value using the predetermined function and the contents of the particular data record.

7. The system of claim 1 wherein the metadata tags generated by the metadata generator of each device include a time stamp.

* * * * *